United States Patent [19]

Audeh

[11] Patent Number: 4,482,744

[45] Date of Patent: Nov. 13, 1984

[54] METHANOL CONVERSION PROCESS

[75] Inventor: Costandi A. Audeh, Princeton, N.J.

[73] Assignee: Mobil Oil Corporation, New York, N.Y.

[21] Appl. No.: 440,894

[22] Filed: Nov. 12, 1982

[51] Int. Cl.³ .................. C07C 149/10; C07C 149/06
[52] U.S. Cl. ........................................ 568/60; 568/69; 568/71; 585/639; 585/640; 585/733
[58] Field of Search ............................ 568/60, 69, 71; 585/639, 640, 733

[56] References Cited

U.S. PATENT DOCUMENTS

| | | | |
|---|---|---|---|
| 2,411,236 | 11/1946 | Thacker | 568/69 |
| 2,829,171 | 4/1958 | Doumani | 568/60 |
| 3,342,879 | 9/1967 | Pine | 585/639 |

FOREIGN PATENT DOCUMENTS 0457938  7/1949  Canada ............................... 585/640

OTHER PUBLICATIONS

B. Fabbi et al., Chem. Abstracts, 1977, 86:143295m.
W. Shanks et al., Chem. Abstracts, 87:71238r.

Primary Examiner—Donald G. Daus
Assistant Examiner—M. C. Eakin
Attorney, Agent, or Firm—Alexander J. McKillop; Michael G. Gilman; Howard M. Flournoy

[57] ABSTRACT

A process is provided wherein methanol is converted over spent shale to products such as mercaptans, disulfides and ethylene.

6 Claims, No Drawings

METHANOL CONVERSION PROCESS

BACKGROUND OF THE INVENTION

1. Field of the Invention

This invention is directed to the conversion of methanol to mercaptans, sulfides, disulfides and ethylene over spent shale. Ethylene is a very desirable product used in the manufacture of polymers. The sulfur compounds so obtained can be used, for example, as odor-giving compounds to natural gas and in the manufacture of solvents. More particularly, the present invention is concerned with a process of which methanol mixed with water and spent shale is converted to other useful compounds.

2. Description of the Prior Art

Spent shale disposal is a major concern in oil shale development because of the volume of material to be disposed of and the potentially harmful materials it contains. Depending on the oil yield from the shale, above ground retorting could require as much as 18.5 tons of oil shale mined per cubic meter of oil produced. Although mining and crushing reduces the oil shale packed density and most of the organic material is removed by retorting, the spent shale volume nevertheless becomes greater than the original volume. Thus, spent shale as a waste product is expected to be available in increasingly large volumes as a result of continually expanding surface retorting operations. The spent shale may be used, for example, in the backfilling of mine areas or other land reclamation operations which are viewed currently as a major avenue for its disposal. Other such uses, as in road construction and as a filler, are also known.

The specific composition and properties of the spent shale depend on where it was obtained as well as on the retorting method by which it was caused to be spent. Generally speaking, oil shale consists of sedimentary inorganic material that contains complex organic materials of high molecular weight sometimes referred to as kerogen. Thermal decomposition is the primary means used to recover liquid products from the oil shale. Pyrolysis, or retorting of the oil shale, yellow gaseous liquid and solid products. The liquid which is produced by the pyrolysis is in the form of vapor or mist as are the non-condensable hydrocarbon gases. The organic carbon which is not recovered as compounds in the gaseous or liquid products is converted to a coke-like deposit and becomes part of the spent shale. The spent shale that remains after retorting of little or no economic value, is the material utilized in this invention.

SUMMARY OF THE INVENTION

It has now been discovered that spent shale can be used in a catalytic manner as a reaction medium over which methanol may be converted into sulfur-containing compounds, various hydrocarbons, particularly $C_1$ to $C_4$ hydrocarbons, and ethylene. The use of waste or spent shale in this manner is therefore highly advantageous.

DESCRIPTION OF SPECIFIC EMBODIMENTS

Having generally described the novel process in accordance herewith, the following is a more specific embodiment thereof.

The novel process of this invention may be briefly described as follows:

1. A sufficient or effective amount of spent shale is placed in a suitable reactor.
2. A methanol/water mixture is charged to the reactor.
3. The reactor is then heated to a reaction temperature, such that when the pressure exceeds 2250 psi, the reactor pressure is released until it returns to 2250 psi. At the end of the reaction, the reactor is cooled to room temperature and vented until the pressure becomes atmospheric.
4.(a) Gas generated as a result of this reaction may be separated into its components by any conveniently known method in the art. For example, methyl mercaptan may be recovered by reaction with sodium hydroxide or potassium hydroxide and then hydrolyzed to the free mercaptan as in equations (1) and (2) below.

In another example, dimethyl sulfide may be recovered by condensation. Dimethyl sulfide is the highly useful raw material for such as the production of dimethylsulfoxide, an industrial solvent, equation (3).

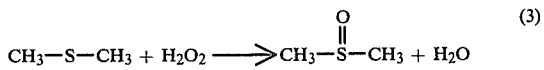

4.(b) Ethylene, one of the gaseous products, may be separated as a gas. Other gases, such as methane are also produced by the reaction.

5. Recycle unconverted methanol.

The temperature of the reactor may vary from about 275° to about 350° C., and preferably from about 300° to 350° C., with 335° C. being more preferred. The pressure of said reactor as stated above, preferably should not exceed 2250 psi, but it may vary from a low of about 1450 to about 2750 psi. Any suitable reactor may be used which can withstand the temperatures and pressures and have sufficient volume for the required process. Reaction time may vary depending upon the amount and the specific nature of the spent shale and the reaction variables usually from 1 to about 4 hours. The methanol-water ratio may vary from 10:1 to about 1:10, although a 1:1 ratio by volume is preferred.

The amount of shale effective for the conversion process will vary depending upon inter alia such factors as the nature of the shale itself, e.g., the amount of sulfur compound contained therein, the method by which it was originally processed, aging and the like. The amount of sulfur is proportional to the pyrite content of raw shale. The amount of shale will also depend upon the method of contacting, for example, a fixed bed operation, an ebullition operation or otherwise. Further, a given quantity of methanol is usually not completely converted and must be recycled. Accordingly, an effective amount of shale for a specific run can be determined by empirical means well-known to those of skill in the art.

EXAMPLE

Seventy-five grams of spent shale were treated with 50 cc of a mixture of methanol and water (1:1 by volume) at 335° C. The reactor was equipped with a backpressure regulator set to open at a pressure of 2250 psi. The gas generated was analyzed and the compounds collected were unreacted methanol, unreacted water, hydrogen sulfide, carbon monoxide, carbon dioxide, methane, ethylene, methyl mercaptan, dimethyl sulfide and minor amounts of various other hydrocarbons.

Although the present invention has been described with preferred embodiments, it is to be understood that modifications and variations may be resorted to without departing from the spirit and scope of this invention, as those skilled in the art will readily understand. Such modifications and variations are considered to be within the purview and scope of the appended claims.

I claim:

1. A method for converting methanol into sulfur-containing compounds, selected from the group consisting essentially of mercaptans, sulfides and disulfides, and $C_1$ to about $C_4$ hydrocarbons comprising contacting from about a 10:1 to about 1:10 ratio by volume of a methanol-to-water mixtue with an effective amount of spent shale in a suitable reaction medium, heating said medium and the materials contained therein to about 275° to 350° C. with the proviso that the pressure not exceed from about 1450 to about 2750 psig for about 1 to 4 hours, and thereafter cooling said reaction medium, separating the products produced therein and recovering said sulfur-containing compounds and hydrocarbons.

2. The method of claim 1 wherein the sulfur-containing products comprise methyl mercaptan and dimethyl sulfide.

3. The method of claim 1 wherein the reaction temperature varies from about 300° C. to 350° C., the pressure varies from about 2000 to 2500 psi and the ratio of methanol to water is about 1:1.

4. The method of claim 1 wherein unreacted methanol is recycled.

5. The method of claim 1 wherein the hydrocarbon is a $C_2$ hydrocarbon.

6. The method of claim 5 wherein the $C_2$ hydrocarbon is ethylene.

* * * * *